| United States Patent [19] | [11] Patent Number: 4,983,382 |
| Wilmott et al. | [45] Date of Patent: Jan. 8, 1991 |

[54] COSMETIC PREPARATION INCORPORATING STABILIZED ASCORBIC ACID

[75] Inventors: James M. Wilmott, West Milford, N.J.; Alexander P. Znaiden, Sloatsburgh, N.Y.

[73] Assignee: Avon Products, Inc., New York, N.Y.

[21] Appl. No.: 291,424

[22] Filed: Dec. 23, 1988

Related U.S. Application Data

[63] Continuation of Ser. No. 7,025, Jan. 27, 1987, abandoned.

[51] Int. Cl.$^5$ .............................................. A61K 7/480
[52] U.S. Cl. ...................................... 424/62; 514/474; 514/947; 514/970
[58] Field of Search ............... 514/474, 724, 738, 947, 514/970; 424/62

[56] References Cited

U.S. PATENT DOCUMENTS

| 2,623,002 | 12/1952 | Fricke | 514/474 |
| 3,322,626 | 5/1967 | D'Argento | 514/474 X |
| 3,954,989 | 5/1976 | Mecca | 424/43 X |
| 4,229,430 | 10/1980 | Yahim et al. | 514/474 X |
| 4,294,852 | 10/1981 | Wildnauer et al. | 514/474 X |
| 4,414,202 | 11/1983 | Silvetti | 514/474 X |
| 4,424,232 | 1/1984 | Parkinson | 514/474 X |
| 4,668,516 | 5/1987 | Duraffourd et al. | 514/474 X |
| 4,818,521 | 4/1989 | Tamabuchi | 514/474 X |

FOREIGN PATENT DOCUMENTS

| 1922653 | 11/1970 | Fed. Rep. of Germany . | |
| 619065 | 3/1949 | United Kingdom | 514/474 |

OTHER PUBLICATIONS

Lehne, "Specialty Polyols", American Perfumer and Cosmetics, vol. 78, Oct. 1963, pp. 103–107.

*Primary Examiner*—Merrell C. Cashion, Jr.
*Assistant Examiner*—Susan S. Rucker
*Attorney, Agent, or Firm*—William G. Todd

[57] ABSTRACT

Stable cosmetic compositions comprising ascorbic acid dissolved in at least two co-solvents, one of which comprises water, the other of which comprises an organic solvent miscible with water, or a blend of water miscible organic solvents. The compositions are adapted to be topically applied to the skin to impart appearance benefits thereto.

10 Claims, No Drawings

COSMETIC PREPARATION INCORPORATING STABILIZED ASCORBIC ACID

This application is a continuation, now abandoned of application Ser. No. 7,025, filed Jan. 27, 1987.

TECHNICAL FIELD

The present invention relates generally to cosmetic preparations, and more specifically to cosmetic preparations incorporating stabilized ascorbic acid (Vitamin C) which topically be applied to human skin to impart beneficial appearance effects thereto.

BACKGROUND ART

It is well known that ascorbic acid (or Vitamin C as it is synonomously referred to herein) is essential to the maintenance of a healthy and attractive skin appearance in humans. Vitamin C helps to stimulate and regulate the production of collagen in human skin tissue thus retarding the formation of wrinkles and otherwise helping to avoid a prematurely aged look to skin which, in turn, helps to maintain a healthier and younger looking appearance longer. Vitamin C also acts to help prevent or minimize lipid oxidation and other forms of cellular damage resulting from prolonged exposure to the sun's ultraviolet rays, further counteracting premature aging of the skin. It is believed further still that ascorbic acid helps to inhibit (i) the formation of melanin which leads to skin discoloration during the aging process, and (ii) the release of histamine from cellular membranes believed to be responsible for many allergenic reactions, particularly among individuals having so-called sensitive skin.

Because of these many beneficial effects, it has long been a desirable objective to percutaneously deliver effective concentrations of ascorbic acid directly to the skin's underlying tissue matrix (i.e. the dermal layer) via a topically applied, cosmetically elegant carrier or base. Although ascorbic acid is readily soluble in water, it oxidizes rapidly in aqueous solutions, and thus cannot be stabilized in sufficient concentration in such media to achieve skin appearance enhancement effects. Solubility of ascorbic acid in non-aqueous media on the other hand is quite limited, thereby preventing an anhydrous base from achieving the desired level of stability and therefore, efficacy For these reasons, unstabilized ascorbic acid heretofore has been used in cosmetic formulas only in trace amounts of less than about 0.1% by weight to serve as an antioxidant, and prior attempts to develop and market an acceptable cosmetic formulation containing efficacious concentrations of stabilized ascorbic acid have failed.

DISCLOSURE OF THE INVENTION

Against the foregoing background, it has been discovered that ascorbic acid, at concentration levels greatly exceeding 0.1% by weight, that is, in the range of about 1% to about 10% by weight, may be stabilized indefinitely in a base or carrier adapted to be toPically applied to the skin. The compositions of the present invention are formed by dissolving the Vitamin C ingredient in a solution comprising at least two co-solvents, one of which is water, the other of which comprises a non-aqueous, organic liquid miscible with water, or a combination of one or more such liquids. The organic liquid co-solvent or solvents preferably are selected to produce a cosmetically elegant formulation which when topically applied to the skin facilitates rapid percutaneous absorption of the stabilized ascorbic acid contained therein whereupon beneficial effects resulting in enhanced skin appearance may be achieved. The amount of water contained in the composition may range as high as 12% by weight without adversely affecting the stability of the ascorbic acid component.

BEST MODE OF CARRYING OUT THE INVENTION

In accordance with the present invention, ascorbic acid (Vitamin C) is stabilized in a cosmetic composition adapted to be topically applied to human skin.

Ascorbic acid, L-ascorbic acid, and/or Vitamin C are the equivalent trivial chemical names given to a white odorless crystalline solid having the formula $C_6H_8O_6$, a molecular weight: 176.13, and the following structural formula:

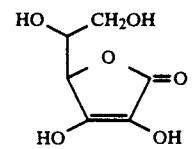

From Table I below it is seen that ascorbic acid is relatively soluble in aqueous% media, but is relatively insoluble in organic solvents such as alcohol, glycol, fats and oils.

TABLE I

| Solubility of Ascorbic Acid (g/mL) | |
|---|---|
| water | 0.33 |
| 95% ethanol | 0.03 |
| absolute ethanol | 0.02 |
| glycerol USP | 0.01 |
| propylene glycol | 0.05 |
| oils | insoluble |
| fats | insoluble |
| fat solvents | insoluble |

Ascorbic acid is notoriously unstable in the presence of oxygen and decomposes rapidly to form L-ascorbic acid 2-hydrogen sulfate and then dehydroascorbic acid. In body cells, the substance glutathione helps to reverse the L-ascorbic acid - dehydroascorbic acid reaction, maintaining a pool of ascorbate distributed throughout the tissues of the body.

In healthy male adults the ascorbate pool is in excess of 1.5 g which would increase to 2.3 to 2.8 g with daily intakes of 200 mg. This pool is located in the plasma and contains 0.8–1.4 mg/100 ml. If the ascorbate pool were to fall below 600 mg, physiological changes would start to occur, and levels below 300 mg would initiate clinical signs of the disease known as scurvy. The human body does not manufacture ascorbic acid and must obtain it from outside sources in order to survive Aside from preventing scurvy, ascorbic acid is essential to many body or biological functions the most notable of which is the synthesis of collagen, the major fibrillar component of dermal connective tissue, comprising approximately 70–80% of the dry weight of the dermis. The collagen fibre molecule consists of amino acid chains wrapped around each other to form a triple helix the formation and stabilization of which depends upon the presence of hydroxylysine and hydroxyproline.

The essential role played by ascorbic acid in the hydroxylation of proline and lysine, hence, in the formation and maintenance of collagen has been investigated widely and is well understood. See, for example, Meanning, J. M., and Meister, A., "Conversion of Proline to Collagen Hydroxyproline", Biochemistry, 5: (4) 1154-1165 (1966); Gottlieb, A. A., Kaplan, A., Udenfriend, S., "Further Evidence for the Accumulation of a Hydroxyproline-deficient, Collagenase-degradable Protein during Collagen Biosynthesis in Vitro", J. Bio. Chem. 241 (7): 1551-1555 (1966); Barnes. M. J., "Function of Ascorbic Acid in Collagen Metabolism", Ann. N.Y. Acad. Sci., 258: 264-277 (1975); Murad, S., Grove, D., Lindberg, K. A., Reynolds, G., Sivarajah, A., Pinnell, S. R., "Regulation of Collagen Synthesis by Ascorbic Acid", Proc. Natl. Acad. Sci. 78 (5): 2879-2882 (1981); and Murad, S., Sivarajah, A., Pinnell, S. R., "Prolyl and Lysyl Hydroxylase Activities of Human Skin Fibroblasts Effect of Donor Age and Ascorbate", J. lnvest. Derm. 75: 404-407 (1980).

More recent studies indicate that ascorbic acid encourages the synthesis of procollagen by stimulating procollagen mRNA. See Freiberger, H., Grove, D., Sivarajah, A., Pinnell, S. R., "Procollagen I Synthesis in Human Skin Fibroblasts: Effect of Culture Conditions on Bi©synthesis", J Invest. Derm. 75: 425-430 (1980); Tajima, S., Pinnell, S. R., "Regulation of Collagen Synthesis B., Ascorbic Acid. Ascorbic Acid Increases Type I Procollagen mRNA", Biochem Biophys Res. Comm. 106 (2): 632-637 (1982); and Murad, S., Tajima, S., Johnson, G.R., Sivarajah, A., Pinnell, S. R., "Collagen Synthesis in Cultured Human Skin Fibroblasts Effects of Ascorbic Acid and Its Anaolgs", J. Invest Derm 81: 158-162 (1983).

Still other studies indicate that ascorbic acid helps increase membrane lipid peroxidation and antioxidation. Girotti, A. W., Thomas, J. P., Jordan, J. E., "Prooxidant and Antioxidant Effects of Ascorbate on Photosenitized Peroxidation of Lipids in Erythrocyte Membranes", photochem. Photobio 41 (3): 267-276 (1985). Ascorbic acid also may help to inhibit the production of melanin responsible for skin discolorations. Tomita, Y., Hariu, A., Mizumo, C., and Seyi, M., "Inactivation of Tyrosinase by Dopa", J. Invest. Derm. 75 (5): 379-382 (1980) Finally, ascorbic acid may prevent the accumulation of histamine in body tissues responsible for many allergenic reactions. Bates, C. J., "The Function and Metabolism of Vitamin C in Man" Vit C Ascorbic Acid, Counsell, J. N., Horninq, D. H., eds., Applied Sci. Publishers Ascorbic levels in humans tend to decrease with age. Collagen levels also decrease accompanied by changes in morphology The fibers become more intermittant and thinner resulting inevitably in surface skin effects such as dryness, flaking, wrinkling and loss of luster and elasticity. See Eyre, D .R. (1980), "Collagen Molecular Diversity in the Body's Protein Scaffold", Science, Vol. 207: 1315-1322; Wright, E. T., Shellow, W. V. (1973), "The Histopathology of wrinkles", J. Soc. Cosmetic Chem. 24: 81-85; and Sinex, F. M. (1968)", "Role of Collagen in Aging", In Treatise on Collagen, Vol 2, Biology of Collagen edited by B. S. Gould, Part B. Academic Press.

Exposure to ultraviolet light also has a tendency to interfere with collagen synthesis causing skin to exhibit the effects of premature aging. See Semma, M., Sasaki M. (1978) "Aging of Skin - Changes of the Dermal Connective Tissue", Cosmetics and Toiletries, Vol. 93:29-36; Bisset. D. L. et al {1986), "An Animal Model of Solar-Aged Skin", Photochem. and Photobiol. Abstracts Vol. 43, Suppl. pp. 955.

We have found in accordance with the present invention that replenishment of the dermal tissues with ascorbic acid delivered percutaneously through the stratum corneum can impart beneficial appearance effects to skin, i.e. improved tone and luster, a decrease in fine lines and Wrinkles, improved elasticity, and so on. As a suitable base or vehicle for the ascorbic acid, a stable composition is provided having desirable cosmetic qualities, namely, an agreeable, pleasant feel and appearance when topically applied to skin.

The stable compositions according to the invention comprise ascorbic acid dissolved in a solution comprising water and at least one organic solvent miscible with water.

The organic solvent must be compatible with water, i.e. it must be polar with one or more hydroxyl groups, and be acceptable for cosmetic use. There are many mono, di, or polyhydric liquids suitable for this purpose including, for example, the alcohols, glycols, and polyols. Without limitation one or more of the following organic solvents may be employed ethanol, N-propynol, isopropyl alcohol, methanol, propylene glycol, butylene glycol, hexylene glycol, glycerine, sorbitol (polyol), di-propylene glycol, and polypropylene glycol. The organic solvent may comprise up to about 90% by weight of the composition.

Ascorbic acid is ever so slightly soluble in propylene glycol, i.e. up to about 4% by weight. However, propylene glycol by itself is not cosmetically elegant due to its oily feel and viscous consistency. Accordingly, a blend of propylene glycol and at least one other organic solvent is preferred With a blend of propylene glycol and ethanol being mostly preferred. When such a blend is employed, the composition may comprise ethanol in the range from about 40% to 90% by weight of the composition and propylene glycol in the range of about 10% to about 50% by weight of the composition. A composition comprising ethanol in the range of about 55% to about 65% by weight and propylene glycol in the range of about 20% to about 25% by weight is especially preferred because of its excellent cosmetic properties, 1.e. such a blend has an elegant feel and appearance.

From Table I it is seen that ascorbic acid is even less soluble in ethanol than it is in propylene glycol (about 2% by weight). The effect of blending ethanol With propylene glycol therefore, is to reduce the solubility level of ascorbic acid in the organic solvent blend. In accordance with the invention, water is added to the organic solvent blend to increase the solubility of ascorbic acid therein. Water may be added up to about 12% by weight without adversely affecting the stability of the ascorbic acid dissolved in the water/organic solvent solute.

Up to about 10% by weight ascorbic acid may be dissolved (and stabilized) in the organic solvent/water composition with the amount of stabilized ascorbic acid varying inversely with respect to the amount of water, i.e. the greater the water content, the less stabilized ascorbic acid in solution.

In a composition comprising by weight about 83% organic solvent blend and about 10% water, we have found that about 5% ascorbic acid may be dissolved and remain stable, and therefore, these proportions are mostly preferred.

It is quite surprising and unobvious that ascorbic acid may be stablized in the compositions of the present invention containing such a relatively high water content or stated otherwise, where water is employed as a co-solvent. U.S. Pat. No. 4,372,874 incorporated herein by this reference, discloses that ascorbic acid may be stabilized in a water miscible organic solvent only if water is removed via a dessicant additive and no more than 0.5% by weight residual water is present.

The foregoing compositions are prepared using techniques well known in the cosmetic arts. The organic solvent or solvent blend, and water are mixed together at room temperature in a suitable, standard mixing vessel. Various other cosmetic ingredients may also be added including emollients, moisturizers, colorants, fragrance, preservatives and antioxidants. Finally, ascorbic acid, preferably in powder form, is added to the mixing vessel under conditions which Will avoid contact with air as, for example, under a hood providing a nitrogen blanket or atmosphere surrounding the mixing vessel. A suitable ascorbic acid ingredient, in powder form, is commercially available from Hoffman La Roche, Nutley, N.J. The final composition may then be packaged in containers for distribution to consumers, preferably in bottles impervious to U.V. light. If desired, the bottles may also be provided with a nitrogen filled headspace The cosmetic compositions of the present invention should provide a stablizing environment for ascorbic acid, be percutaneously adsorptive when topically applied to skin, and impart perceived skin appearance benefits after being applied.

The invention will now be further illustrated and evaluated with respect to meeting the specifications in the preceding paragraph by the folloWing specific examples Which are not to be construed as limiting.

EXAMPLE 1

The following preferred composition was formed by mixing the ingredients together at room temperature under a nitrogen blanket hood.

| Ingredient | % Weight |
| --- | --- |
| ALCOHOL SD 40B | 61.05500% |
| PROPYLENE GLYCOL | 21.00000% |
| HYDROXYPROPYL CELLULOSE | 0.50000% |
| DEMINERALIZED WATER | 10.00000% |
| ASCORBIC ACID-POWDER | 5.00000% |
| PROPYLENE GLYCOL DIPELARGONATE | 1.00000% |
| OCTYL PELARGONATE | 1.00000% |
| C.S. D&C YELLOW NO. 10 (1%) | 0.02500% |
| BUTYLATED HYDROXYTOLUENE | 0.20000% |
| BISABOLOL | 0.20000% |
| PANTHENOL-DL-63920 | 0.20000% |
| TOTAL | 100.00000% |

EXAMPLE 2

A collagen regulation study was performed in accordance with the procedures set forth in Pinnell, S. R.: "Regulation of Collagen Biosynthesis by Ascorbic Acid: A Review"Yale J. Biol. Med. 58: 554–559, (1985); and Tajima, S. and Pinnell, S. R. "Collagen Synthesis by Human Skin Fibroblasts in Culture: Studies of Fibroblasts Explanted From Papillary and Reticular Dermis", J. Invest. Dermatol. 77:410–412, (1981). Normal human skin fibroblasts were seeded into 35 mm tissue culture plates at a density of 100,000 cells per plate and grown in modified Dulbecco media with 20% dialyzed calf serum. Cells were grown to confluent density for 7 days, the media was removed, the cells were washed twice with phosphate buffered saline, and experimental conditions were administered. At this point, cells were density stabilized by carrying out the remainder of the experiment in 0.5% dialyzed calf serum. Media was changed daily and all solutions were made fresh. Conditions were administered for 72 hours and during the last 6 hours of the experiment 2-3,$^3$H-proline 20 uci per plate was added. At the end of the experiment, media and cells were harvested into a cocktail of protease inhibitors and levels of collagen and noncollagen protein were determined by digestion with highly purified bacterial collagenase Cell number was determined by counting in a Coulter counter. Data is expressed in Table II below as the average of duplicate determinations which were conducted on duplicate cultures. The various experimental conditions were:

Condition 1: control (untreated cells)
Condition 2: ascorbic acid 100 uM
Condition 3 composition of Example 1 without ascorbic acid
Condition 4: composition of Example 1 (diluted to final concentration of 100 um ascorbic acid)

TABLE II

|  | Condition 1 | Condition 2 | Condition 3 | Condition 4 |
| --- | --- | --- | --- | --- |
| Collagen synthesis in media cpm/cell | 63.8 | 321.2 | 58.1 | 230.6 |
| Collagen synthesis in pellet cpm/cell | 40.4 | 29.4 | 36.9 | 66.0 |
| % collagen in pellet | 39.0 | 8.3 | 39.0 | 22.0 |
| Total collagen synthesis cpm/cell | 104.2 | 350.6 | 95.1 | 296.6 |
| Total noncollagen synthesis cpm/cell | 927.8 | 1363.0 | 1357.0 | 1051.0 |
| % Protein synthesis devoted to collagen (corrected for increased proline content in collagen) | 2.0 | 4.5 | 1.3 | 5.0 |

DISCUSSION

The results indicate that ascorbic acid enhanced collagen synthesis 3-fold in human skin fibroblasts whether or not the ascorbic acid was dissolved in the vehicle of the composition of Example 1. In the absence of ascorbic acid, collagen is underhydroxylated and incapable of being efficiently secreted from the cell. Under these conditions, an appreciable amount remains in the cell pellet. In the presence of ascorbic acid it is efficiently secreted into the media. This provides a strong indicator of ascorbate response. Ascorbic acid efficiently led to collagen secretion from fibroblasts whether or not it was dissolved in Example 1 vehicle. The study clearly shows that the composition of Example 1 is capable of being presented to cells, of entering cells, and producing the desired response.

CONCLUSION

The composition of Example 1 stimulates human skin fibroblasts to preferentially synthesize collagen in a manner similar to ascorbic acid alone. No evidence was demonstrated that the Example 1 formulation was toxic to cells or changed the ascorbic acid in any way so that it would not be available to exert its specific effect on collagen synthesis within the cell.

EXAMPLE 3

Two separate cosmetic formulations were prepared by mixing the below listed ingredients together Formulation "3A" comprises an ascorbic acid stabilized composition in accordance with the invention and was prepared in the same manner as the composition of Example 1. Formulation "3B" comprises a standard moisturizer night cream.

Table IV summarizes the results of the clinical evaluation made at week 12 of the study.

TABLE III

| Clinical Test Parameters | |
|---|---|
| Parameter | Assessment |
| Visual Texture | When observing the person full face, does one side appear to visually look better, i.e. smoother/softer, less dry? |
| Tactile Texture | Using the back of the hands and concurrently touching each side of the person's face, in an "up/down" motion along the sides, did one side feel softer/smoother (less rough) than the other? |

| % Weight | | |
|---|---|---|
| Formulation 3A | Formulation 3B | Ingredient |
| 60.95500 | — | ALCOHOL SD 40B |
| 21.00000 | — | PROPYLENE GLYCOL |
| .50000 | — | HYDROXYPROPYLCELLULOSE |
| 10.00000 | 65.40000 | DEMINERALIZED WATER |
| 5.00000 | — | ASCORBIC ACID-POWDER |
| 1.00000 | — | PROPYLENE CLYCOL DIPELARGONATE |
| 1.00000 | — | OCTYL PELARGONATE |
| .02500 | — | C.S. D&C YELLOW NO. 10 (1%) |
| .20000 | — | BUTYLATED HYDROXYTOLUENE |
| .02000 | — | BISABOLOL |
| .20000 | .20000 | PANTHENOL-DL-63920 |
| .10000 | .05000 | FRAGRANCE |
| — | .50000 | CARBOPOL 934 |
| — | .20000 | XANTHAN GUM |
| — | 2.50000 | SQUALANE |
| — | .50000 | SQUALENE - PRESERVED |
| — | 8.00000 | MINERAL OIL-LIGHT |
| — | 4.00000 | PETROLATUM |
| — | .50000 | MYRISTYL MYRISTATE |
| — | 1.00000 | ISOPROPYL MYRISTATE |
| — | .80000 | POE FATTY ALCOHOLS |
| — | 3.00000 | STEARIC ACID |
| — | 3.00000 | POE (20 M) MONOSTEARATE |
| — | 3.00000 | ETHYLEHEXYL PALMITATE |
| — | .40000 | METHYLPARABEN |
| — | 1.00000 | CETYL/STEARYL ALCOHOL (60/40) |
| — | .50000 | GLYCERYL MONOSTEARATE |
| — | .25000 | TRIETHANOLAMINE 99% |
| — | .20000 | PROTEIN COLLAGEN-3% AQ |
| — | .20000 | PROTEIN ELASTIN-30% AQ |
| — | .40000 | GERMALL |
| — | .20000 | DISODIUM EDTA |
| — | 4.00000 | LANOLIN ACETATE |
| — | .20000 | TROPOCOLLAGEN/PROCOLLAGEN-PRES. |
| TOTAL 100.00000% | 100.00000% | |

A clinical study was performed to evaluate skin appearance benefits imparted as the result of using the composition of the invention for a period of approximately 3 months. A "split-face" procedure Was used involving a panel of fifty-two (52) female subjects. Each panelist was provided with samples of formulations 3A and 3B and instructed to apply 3A to one side of the face and 3B over the entire face, i.e. both sides. The instructions were designed to provide right/left balance over the entire test panel. Application of the formulations was required twice daily, viz., A.M. and P.M., after cleansing with mild soap and water and towel drying. Observations were made by an experienced Clinician at 2 weeks, 4 weeks, 8 weeks and 12 weeks into the test. A subsequent observation at 14 Weeks was performed by an experienced Dermatologist. The specific parameters observed are set forth in Table III.

| | |
|---|---|
| Pore Size | In persons who had large, visible pores, did the size of the pore appear smaller on one side as opposed to the other; observation areas included the nasal area, cheekbone, chin. |
| Elasticity | Concurrent, gentle "pinching" of the suborbital areas; did the skin "spring" back more quickly on one side as opposed to the other? |
| Lightening | Was pigmentation different, i.e. was one side or one area lighter than the other; areas of observed "lightening" included the whole side of the face or specific areas such as suborbital area or alonq-side cheek. |
| Lines | Areas of observation included crowsfeet and suborbital only; were lines less apparent, appear smoother (less depth) and/or were suborbit areas "less puffy". |

TABLE IV

| | Summary of Clinical Test Results After Week 12 | | | | | | | |
|---|---|---|---|---|---|---|---|---|
| | 2 Wk. (N = 52) | | 4 Wk. (N = 52) | | 8 Wk. (N = 52) | | 12 Wk. (N = 52) | |
| | Treat. (Better) | No Treat. (Better) | Treat. (Better) | No Treat. (Better) | Treat. (Better) | No Treat. (Better) | Treat. (Better) | No Treat. (Better) |
| Visual Texture | 19 (37%) | 1 (2%) | 36 (69%) | 1 (2%) | 26 (50%) | 4 (8%) | 26 (51%) | 6 (12%) |
| Tactile Texture | 13 (25%) | 1 (2%) | 29 (56%) | 1 (2%) | 15 (29%) | 3 (6%) | 24 (47%) | 2 (48%) |
| Pore Size | 9 (17%) | 0 | 13 (25%) | 0 | 17 (33%) | 2 (4%) | 27 (53%) | 5 (12%) |
| Elasticity | 22 (42%) | 2 (4%) | 29 (56%) | 2 (4%) | 21 (40%) | 6 (12%) | 23 (45%) | 3 (6%) |
| Skin Lightening | 0 | 0 | 4 (8%) | 0 | 14 (27%) | 1 (2%) | 25 (49%) | 0 |
| Wrinkles/Lines | 3 (6%) | 0 | 2 (4%) | 0 | 22 (42%) | 4 (8%) | 29 (57%) | 5 (10%) |

DISCUSSION

At the 2 week exam, a few attributes in favor of the side treated with formula 3A emerged, i.e. visual texture, tactile texture, pore size, and elasticity. Although the observed benefit was slight, the difference appeared to be real. After 4 weeks, treated side benefits were more evident in that the number of perceived changes in visual/tactile texture, pore size and elasticity increased; however, the degree of change was again "slight" in the majority of persons. After 8 weeks, visual texture, pore size and elasticity remained basically the same as the 4-week observation in terms of number of persons exhibiting an effect and the degree of change At this exam, two other attributes emerged, viz. skin lightening and a line effect. Although these two benefits were noted in a fair number of persons, the degree of change was slight. At the 12-week and final exam, most benefits remained basically the same as that observed at 8 weeks; an increase in the number of effects were noted for skin lightening, lines and tactile texture. The degree of change for all parameters remained slight. The evaluation conducted by the independent Dermatologist at the end of 14 weeks confirmed the results observed by the Clinician at week 12 A comparison of the assessments made on the same subjects by both the Clinician and the Dermatologist is set forth in Table V.

TABLE V

| | Summary of Clinical Test - 14-Week Dermatological Exam vs. 12-Week Clinical Exam | | | |
|---|---|---|---|---|
| | 14 Wks. Dermatologist (N = 44) | | 12 Wks. Clinician (N = 44) | |
| | Treatment (Better) | No Treatment (Better) | Treatment (Better) | No Treatment (Better) |
| Visual Texture | 10 (23%) | 6 (14%) | 20 (45%) | 5 (11%) |
| Tactile Texture | 19 (43%) | 11 (25%)** | 20 (45%) | 2 (5%) |
| Pore Size | 9 (20%) | 10 (23%) | 21 (48%) | 5 (11%) |
| Elasticity | 9 (20%) | 2% (5%)* | 18 (42%) | 3 (7%) |
| Lines | 18 (41%) | 9% (20%)* | 26 (59%) | 4 (9%) |
| Lightening | 12 (29%) | 5 (12%)** | 21 (48%) | 0 |

*p = <0.05
**p = 0.06

CONCLUSIONS

The clinical observations in this test indicate that treatment by Formulation 3A produces skin benefits in visual/tactile texture, pore size, elasticity, skin lightening and lines in approximately ½ the panel population; although the degree of the benefits observed was considered to be slight. Although the benefits perceived by the Dermatologist were somewhat less than those observed by the Clinican, the dermatological assessment did confirm that the treatment afforded by Formula 3A actually produced skin benefits with respect to lines, elasticity, lightening and tactile texture.

EXAMPLE 4

The effect of Formula 3A {Example 3) on the mechanical properties of skin was evaluated by a panel of 15 females over a use period of one week employing in vivo extensometry. A Cutech in vivo extensometer was utilized This device consists of two arms, one fixed and the other moveable, which are driven apart by a motor driven lead screw. Flat rectangular tabs at the end of the two arms are stuck to the skin surface by means of double-sided adhesive tape and cyanoacrylate. The force exerted on the skin by the fixed and moveable arms is measured by two strain guages attached at reduced sections on each of the two arms. The distance between the tabs is measured by a linear variable differential transformer (LVDT) transducer at the root of the two arms, respectively.

PROCEDURE

Fifteen (15) female Panelists were recruited without regard to age. These volunteers were instructed to wash both forearms twice a day with chip bar and allow to air dry over a period of 14 days. Extensibility assessments were taken before, immediate post-, and 1 hour post-product application. Before and after measures were also taken after 7 days of 1 ×per day product use. Each panelist was assessed by the in vivo extensometer at two different sites. Product was applied with the extensometer feet remaining on the skin surface. The site was then re-evaluated for extensibility and this is defined as the "immediate post-application" point. Extensibility measures were taken again on an equivalent site one hour post-application.

RESULTS

As shown in Table VI, the panel demonstrated a significant increase in the force required to extend the skin 30% after 2 weeks of chip bar washing. These panelists were considered dry on this basis.

TABLE VI

Comparison of Extensibility Values Between Baseline and Chip Bar Washed Forearm Sites
Mean Force Recorded

|  | Baseline | 14 days Chip Bar | Significance |
|---|---|---|---|
| Control Group | 4.02 | 6.84 | $p < 0.001$ |
| Formula 3A | 3.81 | 7.24 | $p < 0.001$ |

Table VII illustrates the results of a single product application. Prior to product application both sets of sites were statistically identical after 1 application of Formula 3A, however, the treated sites require significantly less force for a 30% extension.

TABLE VII

Comparison of Extensibility Values Between Formula 3A Treated and Control Sites After 1 Application
Mean Force Recorded

|  | Pre-treatment | Immediate Post treat | 1 Hour Post-Treat |
|---|---|---|---|
| Control Group | 6.84 | 6.30 | 6.77 |
| Formula 3A | 7.25 | 4.85 | 5.19 |
| Significance | $p > 0.05$ | $p < 0.05$ | $p < 0.02$ |

The results of 7 days of treatment are given in Table VIII. As shown by the data in this table, there is a significant decrease in the force required for the extension after the eighth product application. There was no difference between the pretreatment value on Day 7 and the pretreatment value Day 1, which would have demonstrated a persistent improvement.

TABLE VIII

Comparison of Extensibility Values Between Formula 3A Treated and Control Sites After 7 and 8 Applications
Mean Force Recorded

|  | Pre-treatment (7 applications) | Immediate Post treatment |
|---|---|---|
| Control Group | 5.75 | 5.67 |
| Formula 3A | 5.30 | 3.19 |
| Significance | $p > 0.05$ | $p < 0.001$ |

Tables VII and VIII illustrate that at least a 25% improvement in the force required to deform the skin 30% was achieved for each measured application timepoint.

CONCLUSIONS

The results of this study demonstrate that application of Formula 3A results in a change in the skin's biomechanical properties. Comparison of the force required to extend the skin 30% shows a statistically significant decrease after single and multiple applications. The extensometer used in this study is an established method for assessing the biomechanic 1 properties of the skin. See Gunner, C. W., Hutton, W. C., and T. E. Burlin, (1979), "The Mechanical Properties of Skin In vivo - A Portable Hand-Held Extensometer", Brit. J Derm. 100:161–163; and Marks R. (1983), "Techniques for Measuring the Mechanical Properties of Skin", J. Soc. Cosmet Chem. 34:429–437. The decrease in the force required to extend the skin 30% found with Formula 3A treatment indicates that the skin has become more flexible i.e. is less strained by a deformation.

EXAMPLE 5

A study was conducted to determine whether the composition of Example 1 is percutaneously absorptive when topically applied to human skin.

PROCEDURE

Normal human breast skin was obtained from three unselected patients undergoing mammary reduction as a cosmetic procedure. Breast skin was obtained within one hour of excision and immediately prepared as follows. All subcutaneous fat was removed by scissor excision and the skin was cut with a scalpel into approximately 1.5 × 1.5 cm squares. Each piece of skin was mounted into a glass diffusion chamber having a diameter of 0.9 cm and an available diffusion area of approximately 0.63 cm$^2$. The skin, epidermal side up, was clamped betWeen the upper and lower half of the chamber with a spring loaded column clamp. The dermal side of the chamber was bathed in a solution of 0.9% NaCl, 0.01% sodium azide, 0.4 mM $KH_2PO_4$, 2.0 mM $K_2HPO_4$, pH 7.4. The volume of the lower chamber is standardized for each chamber and varies from 2 6 to 3.4 ml. An attempt was made to minimize all variables by examining all skin specimens carefully for defects during their harvesting. The subcutaneous fat was carefully removed and the skin re-examined at the end of the experiment. Attention was paid to the layering of the solution onto the epidermis, maintenance of hydration of the skin, and prevention of evaporation from the lower chamber.

A 1 ml sample of the composition of Example 1 (5% ascorbic acid solution) was mixed with 5 uCi of L-(carboxyl-C14) ascorbic acid, Amersham code CFA.620 batch 12 with a purity ranging from 96 to 98%. Twenty microliters of the ascorbic acid mixture then was placed on the epidermal surface of the skin mounted in the percutaneous absorption chamber The upper chamber was covered by parafilm and placed in a shaking water bath at 37° C. In some cases the chambers were placed in a 37° C. incubator and stirred with a teflon coated bar by a magnetic stirrer. Results of these two methods were found to be similar. At 72 hours the chambers were removed and duplicate 0.5 ml aliquots were removed from the bottom chamber through the side port. 2.5 ml of scintillation fluid cocktail Aquasol-2 was added and the samples counted in a liquid scintillation counter. An identical 20 lambda of the original solution was counted in 0.5 ml of the bathing solution and 2.5 ml Aquasol-2 by similar means. Cutaneous absorption was calculated as the percentage of radioactivity placed on the epidermal side of the skin which eventually found its way into the bottom chamber bathing fluid.

RESULTS AND DISCUSSION

Based on a weight of 17.2 mg per twenty microliters of the composition of Example 1 and a content of 5% w/w ascorbic acid, approximately 860 ugm ascorbic acid was applied per 0.63 cm$_2$ area. A mean value of 12.8% absorbed or an average of 175 ugm ascorbic acid per cm$^2$ of skin was absorbed as measured over twelve samples for each of the three patients. This study not only demonstrates that the ascorbic acid of the Example 1 composition penetrates human skin and is absorbed into the dermal layer, but furthermore indicates that the amount of ascorbic acid absorbed could be expected to have an impact on dermal collagen synthesis.

EXAMPLE 6

To evaluate the stability of the composition of Example 1, duplicate samples thereof were placed in separate 2 oz. sealed jars with the headspace volumes filled with 3 different atmospheres at three different volumes, viz. oxygen, air, and nitrogen, at 5%, 25% and 50%, respectively (for a total of 18 samples). Ascorbate content in each jar was assayed in accordance with the methodology set forth in the United States Pharmacopia, Vol. XXI, p. 75, "Ascorbic Acid". The jars were sealed after headspace filling under a hood and stored for one month at room temperature and 110° F. The jars were then opened and assayed again using the same method. The results are set forth in Table IX below.

TABLE IX
Ascorbic Acid Stability Test

| Atmos. | % Headsp. | Storage Condition | Ascorbate Stability % weight Init | 1 month |
|---|---|---|---|---|
| O$_2$ | 50 | RT | 5.07 | 3.93 |
|  |  | 110° F. | — | 3.81 |
|  | 25 | RT | 5.07 | 4.55 |
|  |  | 110° F. | — | 4.36 |
|  | 5 | RT | 5.07 | 4.86 |
|  |  | 110° F. | — | 4.79 |
| Air | 50 | RT | 5.07 | — |
|  |  | 110° F. | — | 4.80 |
|  | 25 | RT | 5.07 | — |
|  |  | 110° F. | — | 4.93 |
|  | 5 | RT | 5.08 | — |
|  |  | 110° F. | — | 4.95 |
| N$_2$ | 50 | RT | 5.07 | 5.08 |
|  |  | 110° F. | — | 5.05 |
|  | 25 | RT | 5.07 | — |
|  |  | 110° F. | — | — |
|  | 5 | RT | 5.07 | — |
|  |  | 110° F. | — | — |

Table IX clearly shows that, as expected, under an oxygen environment, ascorbic acid is unstable and decomposes rapidly. However, the Table further shows that when exposed to air or nitrogen, even at elevated temperatures, the ascorbic acid content of the composition studied remained essentially unchanged after one month thereby indicating that the compositions are stable under such conditions.

In practice, the compositions of the present invention may be applied topically, preferably after cleansing the skin area to be affected with mild soap and warm water. It has been found that after application, a standard moisturizing lotion or cream may be applied to the same skin area Without affecting the efficacy of the ascorbic acid composition Which tends to be rapidly percutaneously absorbed by the skin. In fact it has been found that the use of a moisturizer immediately following topical application of the ascorbic acid composition of the present invention, as described above, actually increases the rate of percutaneous absorption of the ascorbic acid ingredient A preferred moisturizer suitable for this purpose is "Accolade Night Treatment", marketed by the independent Representatives of Avon Products, Inc., New York, N.Y.

From the foregoing, it will be appreciated that the present invention discloses stable compositions comprising ascorbic acid which are cosmetically elegant, and which when topically applied to human skin produces actual perceived skin appearance benefits including, but not limited to improvements in luster, tone, and elasticity, and reduction, in fine lines, wrinkles, and pore size. In accordance with the invention, ascorbic acid is stabilized by dissolving the latter in at least two co-solvents, one of which is water, and the other o: which is an organic solvent miscible with water or a blend of such Organic solvents. The resulting compositions as disclosed herein are unobvious, advantageous, and efficacious.

As used herein the terms "solution", "preparation", "composition", "formulation", and "formula" are to be construed interchangeably.

The terms "cosmetic" or "cosmetic preparation" or "cosmetic composition" as used herein, means (i) articles intended to be rubbed, poured, sprinkled, or sprayed on, introduced into, or otherwise applied to the human or animal body or any part thereof for cleaning, beautifying, promoting attractiveness, or altering the appearance, and (ii) articles intended for use as a component of any such articles, e.g. sun screening compositions, medicinal or first aid creams, and so on.

All references cited above are hereby incorporated herein and made part of this specification.

It is desired that the present invention be limited only by the true spirit and scope of the appended claims.

We claim:

1. A stable composition for cosmetic use comprising: ascorbic acid,
a first co-solvent, and
a second co-solvent, said first co-solvent being water, said second co-solvent being an organic solvent, said first and second co-solvents being miscible with each other, said ascorbic acid being present in an amount by weight ranging from about 1% to about 10% and said water being present in an amount by weight ranging up to but no more than about 12%, said second co-solvent comprising the remainder of the composition and being selected from the group consisting of ethanol, N-propynol, isopropyl alcohol, methanol, propylene glycol, butylene glycol, hexylene glycol, glycerine, sorbitol (polyol), di-propylene glycol, polypropylene glycol, or mixtures thereof, said second co-solvent comprising up to but no more than about 90% of the total weight of the composition in which at least about 40% of the total weight of said composition is ethanol, wherein said ascorbic acid is rendered stable in said composition thereby permitting said composition to be topically applied to the skin for facilitating percutaneous absorption of said ascorbic acid relative to the skin effective to produce enhanced skin appearance benefits.

2. The composition of claim 1 wherein said organic solvent comprises a blend of at least two organic solvents miscible with water and each other.

3. The composition of claim 2 wherein said blend of co-solvents comprises a mixture of propylene glycol and ethanol.

4. The composition of claim 1 wherein said ascorbic acid content is about 5% by weight and said water content is about 10% by weight.

5. The composition of claim 3 wherein said ascorbic acid is present in an amount by weight ranging from about 1% to about 10%, said water is present in an amount by weight ranging up to 12%, said propylene glycol is present in an amount by weight ranging form about 20% to about 25% and said ethanol is present in an amount by weight ranging from about 55% to about 65%.

6. The composition of claim 5 wherein said ascorbic acid content is about 5% by weight, and said water content is about 10% by weight.

7. The composition of claim 6 wherein said propylene glycol content is about 20% by weight, said ethanol content is about 62% by weight, and the remainder of the composition comprises one or more emollients, fragrances, antioxidants, and preservatives, or mixtures of the same.

8. The method of improving the appearance of skin comprising the steps of:
   (a) stabilizing ascorbic acid in a cosmetic solution which comprises water and up to about 90% by weight of an organic co-solvent miscible with water wherein at least about 40% of the total weight of said cosmetic solution is ethanol, and
   (b) topically applying said cosmetic solution to the area of skin to be affected such that said ascorbic acid is percutaneously absorbed by said skin.

9. The method of claim 8 comprising the additional step of applying a moisturizer to said area following step (b).

10. The method of claim 8 wherein said cosmetic solution comprises the composition of claim 1.

* * * * *